US009062292B2

(12) United States Patent
Coleman

(10) Patent No.: US 9,062,292 B2
(45) Date of Patent: Jun. 23, 2015

(54) MUTANT T7 POLYMERASES

(75) Inventor: Jack Coleman, East Northport, NY (US)

(73) Assignee: Enzo Life Sciences Inc., Farmingdale, NY (US)

( * ) Notice: Subject to any disclaimer, the term of this patent is extended or adjusted under 35 U.S.C. 154(b) by 242 days.

(21) Appl. No.: 12/807,751

(22) Filed: Sep. 13, 2010

(65) Prior Publication Data

US 2012/0064577 A1    Mar. 15, 2012

(51) Int. Cl.
C12N 9/12    (2006.01)

(52) U.S. Cl.
CPC .................................. *C12N 9/1247* (2013.01)

(58) Field of Classification Search
None
See application file for complete search history.

(56) References Cited

U.S. PATENT DOCUMENTS

| | | | |
|---|---|---|---|
| 5,256,555 A | 10/1993 | Milburn et al. | |
| 5,385,834 A | 1/1995 | Ikeda | |
| 6,586,218 B2 | 7/2003 | Milburn et al. | |
| 6,586,219 B2 | 7/2003 | Milburn et al. | |
| 7,335,471 B2 | 2/2008 | Guillerez et al. | |
| 7,507,567 B2 | 3/2009 | Sugiyama et al. | |
| 2006/0063154 A1 | 3/2006 | McAllister et al. | |

FOREIGN PATENT DOCUMENTS

EP        1403364        3/2004

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Altschul et al., Protein database searches using compositionally adjusted substitution matrices, FEBS Journal 2005, 5101-5109, 272.
Altschul et al., Gapped BLAST and PSI-BLAST: a new generation of protein database search programs, Nucleic Acids Research, 1997, 3389-3402, 25.
Brieba, Luis G. and Sousa, Rui, Roles of Histidine 784 and Tyrosine 639 in Ribose Discrimination by T7 RNA Polymerase, Biochemistry 2000, 919-923, 39.
Chelliserrykattil et al., A combined in vitro / in vivo selection for polymerases with novel promoter specificities, BMC Biotechnology 2001, 13, 1.
Cunningham, Philip R. and Ofengand, James, Use of inorganic pyrophosphatase to improve the yield of in vitro transcription reactions catalyzed by T7 RNA polymerase, Biotechniques, 1990,713-714, 9.
Dunn, John J., and Studier, F. William, Nucleotide Sequence from the Genetic Left End of Bacteriophage T7 DNA to the Beginning of Gene 4, .J. Mol Biol. 1981, 303-330, 148.
Ellinger, Thomas and Ehricht, Ralf, Single-Step Purification of T7 RNA Polymerase with a 6-Histidine Tag, BioTechniques 1998, 718-720, 24.
He, Biao, A gene expression system based on bacteriophage RNA polymerases and characterization of bacteriophage T7 RNA polymerase, Thesis/Dissertation, 1996, SUNY New York Health Sciences Center at Brooklyn, NY.

Izawa et al., Recognition Sites of 3*-OH Group by T7 RNA Polymerase and Its Application to Transcriptional Sequencing, The Journal of Biological Chemistry 1998, 14242-14246, 273.
Joyce, Catherine M., Choosing the right sugar: How polymerases select a nucleotide substrate, Proc. Natl. Acad. Sci. USA 1997, 1619-1622, 94.
Kostyuk et al., Mutants of T7 RNA polymerase that are able to synthesize both RNA and DNA, FEBS Letters 1995, 165-168, 369.
Liakhov et al., Site-specific mutagenesis of residue Lys-172 of phage T7 RNA polymerase: characterization of transcription properties of mutant proteins, Mol Biol (Mosk). 1992, 1022-1035, 26, Abstract only.
Lyakhov et al., Mutant Bacteriophage T7 RNA Polymerases with Altered Termination Properties, J. Mol. Biol. 1997, 28-40, 269.
Macdonald et al., Characterization of two types of termination signal for bacteriophage T7 RNA polymerase, J Mol. Biol. 1994, 145-158, 238.
Padilla, Robert and Sousa, Rui, A Y639F/H784A T7 RNA polymerase double mutant displays superior properties for synthesizing RNAs with non-canonical NTPs, Nucleic Acids Research, 2002, e138, 30.
Stahl, Stephen J. and Zinn, Kai, Nucleotide Sequence of the Cloned Gene for Bacteriophage T7 RNA Polymerase, J. Mol. Biol. 1981, 481-485, 148.
Tunitskaya, V.L. and Kochetkov, S.N., Structural-Functional Analysis of Bacteriophage T7 RNA Polymerase, Biochemistry (Moscow), 2002, 1124-1135, 67 Translated from Biokhimiya, 2002,1360-1373, 67.
Van Gelder et al., Amplified RNA synthesized from limited quantities of heterogeneous cDNA, Proc. Nati. Acad. Sci. USA 1990,1663-1667, 87.
Wang et al., High-fidelity mRNA amplification for gene profiling, Nature Biotechnology 2000, 457-459, 18.
Yang, Xiao-Ming and Richardson, Charles C., Amino Acid Changes in a Unique Sequence of Bacteriophage T7 DNA Polymerase Alter the Processivity of Nucleotide Polymerization, J Biol, Chem., 1997, 6599-6606, 272.
Sampson et al., "Biochemical and physical characterization of an unmodified yeast phenylalanine transfer RNA transcribed *in vitro*," *Proc. Natl. Acad. Sci.*, vol. 85, pp. 1033-1037 (1988).
Tabor et al., "DNA Sequence Analysis with a Modified Bacteriophage T7 DNA Polymerase," *The Journal of biological Chemistry*, vol. 265, No. 14, pp. 8322-8328 (1990).
Weitzmann et al., Cloning, *in vitro* transcription, and biological activity of *Escherichia colii* 23S ribosomal RNA, *Nuclic Acids Research*, vol. 18, No. 12, pp. 3515-3520 (1990).

* cited by examiner

*Primary Examiner* — Richard Hutson
(74) *Attorney, Agent, or Firm* — Anna D. DiGabriele Petti

(57) ABSTRACT

Provided are mutant polymerases that comprise a deletion of at least four amino acids among the amino acids at positions corresponding to 167-174 of SEQ ID NO:1. Also provided are mutant polymerases having greater resistance to 30 mM NaCl, 7.5 mM phosphate, or 20 µg/ml single stranded DNA than a wild-type T7 RNA polymerase having SEQ ID NO:1 or a wild-type T3 RNA polymerase having SEQ ID NO:3. Nucleic acids comprising a nucleotide sequence encoding any of the above mutant polymerases are also provided, as are vectors comprising those nucleic acids and host cells transformed with the vectors Additionally, methods of amplifying mRNA using the mutant polymerases described herein are also provided. Further, compositions comprising any of the mutant polymerases described herein, and a reagent at a concentration that is inhibitory to wild-type T7 RNA polymerase is provided.

12 Claims, 3 Drawing Sheets

Identities = 726/884 (82%), Positives = 795/884 (89%), Gaps = 1/884 (0%)

```
T3    1    MNIIENIEKNDFSEIELAAIPFNTLADHYGSALAKEQLALEHESYELGERRFLKMLERQA    60
T7    1    MNTI-NIAKNDFSDIELAAIPFNTLADHYGERLAREQLALEHESYEMGEARFRKMFERQL    59

T3   61    KAGEIADNAAAKPLLATLLPKLTTRIVEWLEEYASKKGRKPSAYAPLQLLKPEASAFITL   120
T7   60    KAGEVADNAAAKPLITTLLPKMIARINDWFEEVKAKRGKRPTAFQFLQEIKPEAVAYITI   119

T3  121    KVILASLTSTNMTTIQAAAGMLGKAIEDEARFGRIRDLEAKHFKKHVEEQLNKRHGQVYK   180
T7  120    KTTLACLTSADNTTVQAVASAIGRAIEDEARFGRIRDLEAKHFKKNVEEQLNKRVGHVYK   179

T3  181    KAFMQVVEADMIGRGLLGGEAWSSWDKETTMHVGIRLIEMLIESTGLVELQRHNAGNAGS   240
T7  180    KAFMQVVEADMLSKGLLGGEAWSSWHKEDSIHVGVRCIEMLIESTGMVSLHRQNAGVVGQ   239

T3  241    DHEALQLAQEYVDVLAKRAGALAGISPMFQPCVVPPKPWVAITGGGYWANGRRPLALVRT   300
T7  240    DSETIELAPEYAEAIATRAGALAGISPMFQPCVVPPKPWTGITGGGYWANGRRPLALVRT   299

T3  301    HSKKGLMRYEDVYMPEVYKAVNLAQNTAWKINKKVLAVVNEIVNWKNCPVADIPSLERQE   360
T7  300    HSKKALMRYEDVYMPEVYKAINIAQNTAWKINKKVLAVANVITKWKHCPVEDIPAIEREE   359

T3  361    LPPKPDDIDTNEAALKEWKKAAAGIYRLDKARVSRRISLEFMLEQANKFASKKAIWFPYN   420
T7  360    LPMKPEDIDMNPEALTAWKRAAAAVYRKDKARKSRRISLEFMLEQANKFANHKAIWFPYN   419

T3  421    MDWRGRVYAVPMFNPQGNDMTKGLLTLAKGKPIGEEGFYWLKIHGANCAGVDKVPFPERI   480
T7  420    MDWRGRVYAVSMFNPQGNDMTKGLLTLAKGKPIGKEGYYWLKIHGANCAGVDKVPFPERI   479

T3  481    AFIEKHVDDILACAKDPINNTWWAEQDSPFCFLAFCFEYAGVTHHGLSYNCSLPLAFDGS   540
T7  480    KFIEENHENIMACAKSPLENTWWAEQDSPFCFLAFCFEYAGVQHHGLSYNCSLPLAFDGS   539

T3  541    CSGIQHFSAMLRDEVGGRAVNLLPSETVQDIYGIVAQKVNEILKQDAINGTPNEMITVTD   600
T7  540    CSGIQHFSAMLRDEVGGRAVNLLPSETVQDIYGIVAKKVNEILQADAINGTDNEVVTVTD   599

T3  601    KDTGEISEKLKLGTSTLAQQWLAYGVTRSVTKRSVMTLAYGSKEFGFRQQVLDDTIQPAI   660
T7  600    ENTGEISEKVKLGTKALAGQWLAYGVTRSVTKRSVMTLAYGSKEFGFRQQVLEDTIQPAI   659

T3  661    DSGKGLMFTQPNQAAGYMAKLIWDAVSVTVVAAVEAMNWLKSAAKLLAAEVKDKKTKEIL   720
T7  660    DSGKGLMFTQPNQAAGYMAKLIWESVSVTVVAAVEAMNWLKSAAKLLAAEVKDKKTGEIL   719

T3  721    RHRCAVHWTTPDGFPVWQEYRKPLQKRLDMIFLGQFRLQPTINTLKDSGIDAHKQESGIA   780
T7  720    RKRCAVHWVTPDGFPVWQEYKKPIQTRLNLMFLGQFRLQPTINTNKDSEIDAHKQESGIA   779

T3  781    PNFVHSQDGSHLRMTVVYAHEKYGIESFALIHDSFGTIPADAGKLFKAVRETMVITYENN   840
T7  780    PNFVHSQDGSHLRKTVVWAHEKYGIESFALIHDSFGTIPADAANLFKAVRETMVDTYESC   839

T3  841    DVLADFYSQFADQLHETQLDKMPPLPKKGNLNLQDILKSDFAFA   884
T7  840    DVLADFYDQFADQLHESQLDKMPALPAKGNLNLRDILESDFAFA   883
```

FIG. 1

MUTANT T7 POLYMERASES

BACKGROUND OF THE INVENTION (1) Field of the Invention

The present invention generally relates to improved enzymes for molecular biology. More specifically, mutant RNA polymerases are provided that have improved resistance to common reagents including phosphate.

(2) Description of the Related Art

RNA and DNA polymerization reactions, which result in the synthesis of RNA or DNA polynucleotides, are an integral part of a variety of techniques used in molecular biology. Such reactions include in vitro transcription and amplification techniques such as the polymerase chain reaction (PCR), RNA amplification and self-sustained sequence replication. These reactions often employ RNA polymerases, especially bacteriophage RNA polymerases such as SP6, T7 and T3, for example, in the synthesis of both labeled RNA probes and unlabeled RNA. Improved performance of the RNA polymerases utilized in these reactions would thus be beneficial.

The rate of these synthetic reactions, and the amount of product formed, is limited by several factors. Lowering the magnesium concentration and salt concentration allows the use of high concentrations of substrate nucleotides and improve the yields of a transcription reaction (U.S. Pat. Nos. 6,586,219, 6,586,218 and 5,256,555). Those techniques prevent inhibition caused by some reaction substrates, but inhibition by other substrates and reaction products, e.g., phosphate, pyrophosphate and single stranded DNA (ssDNA) can still inhibit polymerase activity.

Transcription reactions and DNA polymerase and DNA sequencing applications routinely use the enzyme inorganic pyrophosphatase since addition of that enzyme improves the yield of transcription reactions by removing pyrophosphate (Sampson & Uhlenbeck, 1988; Weitzmann et al., 1990; Cunningham & Ofengand, 1990; Tabor & Richardson, 1990). Pyrophosphatase cleaves the polymerase reaction product pyrophosphate to produce two molecules of phosphate. However, phosphate inhibits RNA polymerase, especially at high concentrations. For example, the optimal total concentration of nucleotides found by Cunningham & Ofengand (1990) of 16 mM produces 32 mM phosphate at the end of the reaction, which is inhibitory to RNA polymerase.

Although there are various protocols in molecular biology where reactions utilizing more than one enzyme are combined, the inhibition of RNA polymerases by reagents such as pyrophosphate and phosphate can thwart efforts to simplify protocols. For example, a typical protocol for amplification of mRNA involves synthesizing a first strand cDNA using reverse transcriptase, followed by a second strand cDNA synthesis using DNA polymerase, then RNA transcription from the cDNA using RNA polymerase. See, e.g., Wang et al., 2000. These protocols usually require a cDNA purification step after the second strand synthesis because buffers and reaction products present from the cDNA synthesis procedures inhibit the RNA polymerase. Some second strand synthesis buffers are available that do not have phosphate, but an RNA polymerase that is not inhibited by phosphate would make their use, or a cDNA purification step, unnecessary.

One of the characteristics of wild-type T7 RNA polymerase is the ability to carry out some level of promoter independent synthesis by using the 3' ends of single-stranded DNA as an initiation site. For in vitro transcription reactions, substrates that give this synthesis can be DNA primers and double-stranded linearized DNA with single-stranded 3' tails. This can especially be a problem when there are large amounts of primers present and low levels of promoter templates. This can also take place with low amounts of RNA analyte samples where single-stranded carrier DNA has been added to increase efficiency of recovery. As a consequence of this property, there can be a large amount of aberrant synthesis taking place even in the complete absence of any input RNA, thus implying that at low levels of legitimate targets, a large amount of labeled product is only contributing to background and not signal. Secondly, the formation of this promoter independent synthesis uses up reagents such that the net yield of legitimate product can be decreased by competition with the promoter independent synthesis.

A number of mutations in RNA polymerases that modify characteristics of those enzymes are known. For example, certain mutations in T7 RNA polymerase ("T7") (e.g., Y639F/S641A; del172-173; F644Y; F667Y) allow the polymerase to utilize deoxyribonucleotides along with ribonucleotides as substrates (Kostyuk et al., 1995; Izawa et al., 1998; European Patent Application EP1403364A1). See also Joyce (1997), Izawa et al. (1998) and Brieba and Sousa (1999). Other mutations increase (e.g. K172L, Del172-173, K98R) or decrease (e.g., P266L) promoter binding strength (Tunitskaya and Lochetkov, 2002; U.S. Pat. No. 7,335,471) or alter the termination properties of the enzyme (e.g., del 163-164, R173C). See Lyakhov et al. (1992), Lyakhov et al. (1997), Tunitskaya and Lochetkov (2002). Still other mutations (e.g., N748D, N748Q, Q758C, E222K, R756M) alter promoter recognition (U.S. Pat. No. 5,385,834; Chilliserrylattil et al., 2001) or increase the thermostability of the enzyme (e.g., S430P, F849I, F880Y, S633P—U.S. Pat. No. 7,507,567). Additional T7 mutations are described in He (1996), Macdonald et al. (1994), and Yang and Richardson (1997).

Mutations analogous to some of the above mutations have been effectively made in T3 RNA polymerase ("T3") (see, e.g., Lyakhov et al., 1997 and European Patent Application No. EP1403364), demonstrating that the various domains of these related phage RNA polymerases are functionally equivalent.

The present invention provides, in part, RNA polymerase mutants with improved characteristics, including resistance to phosphate, pyrophosphate, sodium chloride, and/or single stranded DNA that can be advantageously used in place of wild-type RNA polymerases for various molecular biology procedures.

BRIEF SUMMARY OF THE INVENTION

The present invention is directed to mutant RNA polymerases with particular deletions that confer resistance to various reagents, including phosphate, pyrophosphate, sodium chloride, and/or single stranded DNA.

Thus, in some embodiments, mutant polymerases are provided that comprise a deletion of at least four amino acids among the amino acids at positions corresponding to 167-174 of SEQ ID NO:1.

Also provided are mutant polymerases having greater resistance to 30 mM NaCl, 7.5 mM phosphate, or 20 µg/ml single stranded DNA than a wild-type T7 RNA polymerase having SEQ ID NO:1 or a wild-type T3 RNA polymerase having SEQ ID NO:3.

Additionally, nucleic acids comprising a nucleotide sequence encoding any of the above mutant polymerases are provided.

Further provided are vectors comprising the above nucleic acids.

In other embodiments, host cells transformed with the above vectors are provided.

In additional embodiments, methods of amplifying mRNA are provided. The methods comprise (a) combine the mRNA with a reverse transcriptase and an appropriate first buffer and first reagents to form a first mixture and incubate the first mixture under conditions and for a time sufficient to synthesize a first strand of a cDNA; (b) form a second mixture by adding (i) DNA polymerase or an RNA polymerase having DNA polymerase activity and (ii) an appropriate second buffer and second reagents to the first mixture comprising the first strand cDNA, and incubating the second mixture under conditions and for a time sufficient to synthesize a second strand of the cDNA and form a double stranded cDNA (ds-cDNA); and (c) form a third mixture by adding an appropriate third buffer, third reagents and any of the mutant polymerases described herein to the second mixture comprising the ds-cDNA, and incubating the third mixture under conditions and for a time sufficient to synthesize a needed amount of amplified RNA.

In further embodiments, a composition is provided. The composition comprises any of the mutant polymerases described herein, and a reagent at a concentration that is inhibitory to wild-type T7 RNA polymerase, wherein the reagent is a salt, phosphate, pyrophosphate or single stranded DNA.

BRIEF DESCRIPTION OF THE DRAWINGS

FIG. 1 is a sequence alignment of the amino acid sequences of T3 RNA polymerase (SEQ ID NO:3) and T7 RNA polymerase (SEQ ID NO:1).

DETAILED DESCRIPTION OF THE INVENTION

Figure 2:
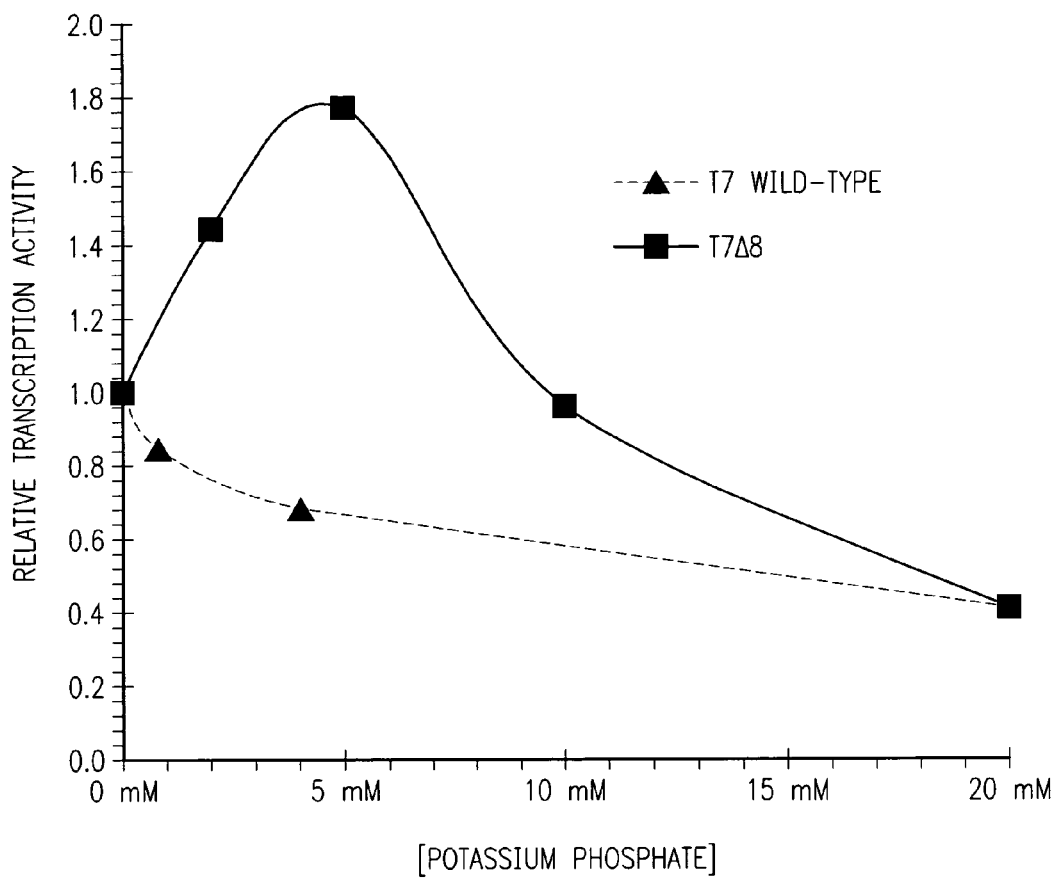
FIG. 2 is a graph comparing relative transcription activity of wild-type T7 polymerase with the mutant polymerase T7Δ8 in the presence of varying concentrations of potassium phosphate.

As used herein, the singular forms "a", "an" and "the" are intended to include the plural forms as well, unless the context clearly indicates otherwise. Additionally, the use of "or" is intended to include "and/or", unless the context clearly indicates otherwise.

The present invention is based in part on the discovery of a region of phage RNA polymerases that confer susceptibility to reagents that are commonly used in molecular biology protocols, such as phosphate, pyrophosphate, sodium chloride (NaCl), and single stranded DNA (ssDNA). That region is defined by amino acids 167-174 of T7 RNA polymerase ("T7"; SEQ ID NO:1) or corresponding regions of related phage RNA polymerases. As such, deletions of at least four amino acids in that region are useful in imparting resistance to those reagents. See Example 1, demonstrating that a mutant of T7 having a deletion of amino acids 167-174 of SEQ ID NO:1 is more resistant to phosphate, pyrophosphate, NaCl, and ssDNA than wild type T7. That mutant, designated T7Δ8, has the amino acid sequence of SEQ ID NO:2. It is believed that a deletion of any 4 of the amino acids in positions corresponding to 167-174 would result in an RNA polymerase that is more resistant to phosphate, pyrophosphate, NaCl, or single stranded DNA than wild type T7 RNA polymerase Thus, in some embodiments, mutant polymerases are provided that comprise a deletion of at least four amino acids among the amino acids at positions corresponding to 167-174 of SEQ ID NO:1.

As used herein, amino acids corresponding to 167-174 of SEQ ID NO:1 are the amino acid residues from a second RNA polymerase sequence that align with amino acids 167-174 of SEQ ID NO:1 when SEQ ID NO:1 is aligned with the amino acid sequence of the second RNA polymerase using the computer program BLASTP 2.2.24+ or an equivalent program (Altschul et al., 1997; 2005). In such an alignment, it is recognized that there may not be 8 amino acid residues from the second RNA polymerase that align with 167-174 of SEQ ID NO:1, since the BLASTP program may confer a gap in the 167-174 region either in SEQ ID NO:1 (in which case there would be more than 8 corresponding amino acids) or in the sequence of the second RNA polymerase in that area (in which case there would be less than 8 corresponding amino acids).

In various embodiments, the mutant RNA polymerase comprises a deletion of 5, 6, 7 or 8 amino acids among the amino acids at positions corresponding to 167-174 of SEQ ID NO:1.

Numerous naturally occurring RNA polymerases have sufficient homology to SEQ ID NO:1 (e.g., at least 30%, at least 32%, at least 37%, at least 38%, at least 50%, at least 60%, at least 70%, or at least 80%) that the skilled artisan would understand that those polymerases have a region functionally equivalent to the region at 167-174 of SEQ ID NO:1. Table 1 provides a listing of such known RNA polymerases, including the homology of those RNA polymerases to T7 (SEQ ID NO:1) as well as the number of residues at the region equivalent to amino acids 167-174 of SEQ ID NO:1 that are identical, or identical + having conserved substitutions to that region of SEQ ID NO:1. As is known in the art, a "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall peptide retains its spacial and charge conformation. For example, common conserved changes are Asp to Glu, Asn or Gln; His to Lys, Arg or Phe; Asn to Gln, Asp or Glu and Ser to Cys, Thr or Gly. For the purpose of the conserved substitution, the 20 essential amino acids can be grouped as follows: alanine, valine, leucine, isoleucine, proline, phenylalanine, tryptophan and methionine having nonpolar side chains; glycine, serine, threonine, cystine, tyrosine, asparagine and glutamine having uncharged polar side chains; aspartate and glutamate having acidic side chains; and lysine, arginine, and histidine having basic side chains.

TABLE 1

Comparison of T7 RNA polymerase with other RNA polymerases[1]

| Source | Genbank # | Homology to T7[2] | Identity to T7 at 167-174[3] | Identity + conserved substitutions at 167-174[4] |
|---|---|---|---|---|
| *Enterobacteria* 13a | ACF15888.1 | 98% | 8/8 | 8/8 |
| *Yersinia pestis* ΦA1122 | AAP20500 | 98% | 8/8 | 8/8 |
| *Salmonella* Vi06 | CBV65202.1 | 93% | 8/8 | 8/8 |
| *Salmonella* ΦSG-JL2 | ACD75668.1 | 82% | 7/8 | 7/8 |
| *Yersinia* ΦY303-12 | CAB63592.1 | 82% | 7/8 | 7/8 |
| *Enterobacteria* T3 | CAC86264.1 | 82% | 7/8 | 7/8 |
| *Enterobacteria* 285P | ACV32460.1 | 76% | 6/8 | 7/8 |
| *Kluyvera* Kvp1 | ACJ14548.1 | 76% | 6/8 | 7/8 |
| *Enterobacteria* BA14 | ACF15731.1 | 76% | 6/8 | 7/8 |
| *Yersinia* Berlin | CAJ70654.1 | 75% | 6/8 | 7/8 |
| *Yersinia* Yep2 | ACF15684.1 | 75% | 6/8 | 7/8 |
| *Klebsiella* K11 | ACF15837.1 | 73% | 5/8 | 7/8 |
| *Enterobacteria* K11 | CAA37330.1 | 72% | 5/8 | 7/8 |
| *Morganella* MmP1 | ACY74627.1 | 71% | 6/8 | 6/8 |
| *Enterobacteria* K1F | AAZ72968.1 | 62% | 4/8 | 5/8 |
| *Enterobacteria*EcoDS1 | ACF15785.1 | 62% | 4/8 | 5/8 |
| *Vibrio* N4 | ACR16468.1 | 61% | 3/8 | 5/8 |
| *Vibrio* VP4 | AAY46276.1 | 61% | 3/8 | 5/8 |
| *Pseudomonas* gh-1 | AAO73140.1 | 57% | 2/8 | 5/8 |
| *P. pudita* KT2440 | AAN67879.1 | 38% | 4/8 | 5/8 |
| *Agrobacterium tumefaciens* C58* | AAK86987.1 | 37% | 3/8 | 4/8 |
| *Azorhizobium caulinodans* ORS 571* | BAF89605.1 | 35% | 0/8 | 3/8 |
| *Enterobacteria* SP6 | AAR90000.1 | 32% | 1/8 | 3/8 |
| *Enterobacteria* Sf6 | CAA68288.1 | 32% | 1/8 | 3/8 |
| *Burkholderia thailandensis* MSMB43* | ZP_02468154.1 | 32% | 1/8 | 3/8 |
| *Enterobacteria* K1-5 | AAL86891.1 | 32% | 1/8 | 3/8 |
| *Enterobacteria* K1E | CAJ29407.1 | 32% | 1/8 | 3/8 |
| *Ralstonia* RSB1 | BAG70384.1 | 31% | 2/8 | 4/8 |
| *Xanthomonas* ΦL7 | ACE75775.1 | 31% | 1/8 | 3/8 |
| *Erwinia* Era103 | ABM63398.1 | 31% | 1/8 | 3/8 |
| *Pyramidobacter piscolens* W5455* | EFB89737.1 | 30% | 1/8 | 1/8 |

[1]RNA polymerases having at least 30% amino acid identity to T7 when aligned using BLASTP 2.2.24+. All RNA polymerases listed are bacteriophage polymerases, unless indicated by an asterisk (*).
[2]Amino acid identity to T7 when aligned using BLASTP 2.2.24+.
[3]Number of identical amino acid residues to T7 at region corresponding to 167-174 of wild-type T7 when the amino acid sequence is aligned to the wild-type T7 amino acid sequence using BLASTP 2.2.24+.
[4]Number of identical and conserved amino acid residues to T7 at region corresponding to 167-174 of wild-type T7 when the amino acid sequence is aligned to the wild-type T7 amino acid sequence using BLASTP 2.2.24+.

A commonly used RNA polymerase that is closely related to T7 is T3 RNA polymerase ("T3"), having the amino acid sequence of SEQ ID NO:3. As indicated in Table 1, T3 is 82% identical to T7 and has 7 of 8 amino acids identical to 167-174 of T7 in the region corresponding thereto. See FIG. 1, showing an alignment of the amino acid sequences of T3 with T7 (SEQ ID NO:3 and SEQ ID NO:1, respectively), where amino acids 167-174 (deleted in T7Δ8) of T7 and the corresponding region of T3 (amino acids 168-175) are bold-underlined. As such, the skilled artisan would understand that a deletion of 4, 5, 6, 7 or 8 amino acids of T3 within the region corresponding to 167-174 of T7 (i.e., within amino acids 168-175 of SEQ ID NO:3) would confer greater resistance to phosphate, pyrophosphate, NaCl, and/or ssDNA than wild type T3. Thus, in determining whether an RNA polymerase has a region corresponding to 167-174 of T7 to assess whether a deletion could be made to confer resistance to phosphate, pyrophosphate, NaCl, and/or ssDNA, the skilled artisan could evaluate the homology of the RNA polymerase in question with either T7 (SEQ ID NO:1) or T3 (SEQ ID NO:3). Thus, in some embodiments, the mutant polymerase of the present invention comprises an amino acid sequence having at least about 30% amino acid homology to SEQ ID NO:1 or SEQ ID NO:3. In other embodiments, the mutant polymerase comprises an amino acid sequence having at least about 50% amino acid homology to SEQ ID NO:1 or SEQ ID NO:3. In still other embodiments, the mutant polymerase comprises an amino acid sequence having at least about 60% amino acid homology to SEQ ID NO:1 or SEQ ID NO:3. In further embodiments, the mutant polymerase comprises an amino acid sequence having at least about 70% amino acid homology to SEQ ID NO:1 or SEQ ID NO:3. In still further embodiments, the mutant polymerase comprises an amino acid sequence having at least about 80% amino acid homology to SEQ ID NO:1 or SEQ ID NO:3. In even further embodiments, the mutant polymerase comprises an amino acid sequence having at least about 90% amino acid homology to SEQ ID NO:1 or SEQ ID NO:3. In additional embodiments, the mutant polymerase comprises an amino acid sequence having at least about 95% amino acid homology to SEQ ID NO:1 or SEQ ID NO:3. In still additional embodiments, the mutant polymerase comprises an amino acid sequence having at least about 98% amino acid homology to SEQ ID NO:1 or SEQ ID NO:3. In still further embodiments, the mutant polymerase comprises an amino acid sequence having at least about 99% amino acid homology to SEQ ID NO:1 or SEQ ID NO:3. Further, the mutant polymerase can comprise the amino acid sequence of SEQ ID NO:1 or SEQ ID NO:3, except for the deletion.

When determining whether any particular RNA polymerase has a region functionally equivalent to the region at 167-174 of SEQ ID NO:1, the skilled artisan might also take into account the number of amino acids that are identical, or identical + conserved to 167-174 of SEQ ID NO:1 at the corresponding region of the RNA polymerase in question. For example, the skilled artisan would consider an RNA polymerase with at least 1/8, at least 2/8, at least 3/8, at least 4/8, at least 5/8, at least 6/8, or at least 7/8 identical, or identical + conserved amino acids, or any combination thereof, in the region corresponding to 167-174 of SEQ ID NO:1 as strong evidence that the corresponding region of that RNA polymerase is functionally equivalent to 167-174 of SEQ ID NO:1, such that a deletion of at least 4 amino acids in that corresponding region of the RNA polymerase in question would be likely to confer resistance to phosphate, pyrophosphate, NaCl and/or ssDNA.

In various embodiments, the mutant polymerase of the present invention is more resistant to phosphate, pyrophosphate, NaCl, and/or ssDNA than the same polymerase not having the deletion in the region corresponding to 167-174 of SEQ ID NO:1. In some of these embodiments, the polymerase has greater resistance to 30 mM, or 20 mM, or 10 mM or 5 mM NaCl; 10 mM, or 7.5 mM, or 5 mM, or 2.5 mM, or 1 mM phosphate; 10 mM, or 7.5 mM, or 5 mM, or 2.5 mM, or 1 mM pyrophosphate; or 20 µg/ml ssDNA than the same polymerase not having the deletion. In other of these embodiments, the polymerase has greater resistance to 30 mM NaCl, 7.5 mM phosphate, 7.5 mM pyrophosphate, or 20 µg/ml ssDNA than wild-type T7 RNA polymerase having SEQ ID NO:1 or wild-type T3 RNA polymerase having SEQ ID NO:3.

The mutants of the present invention also have the property that competition with promoter-independent synthesis by single-stranded DNA is reduced compared to the wild type enzyme. In some cases, not only is synthesis resistant to inhibition by single-stranded DNA competitor but there may be a stimulatory effect for synthesis of the legitimate promoter-driven target.

In some embodiments, the mutant polymerase further comprises at least one additional mutation. The additional mutation can be any mutation now known or later discovered. Nonlimiting examples of known useful mutations that can be present in the mutant polymerase of the present invention include mutations corresponding to the following mutations in SEQ ID NO:1: Y639F, S641A, F644Y, F667Y, E222K, S430P, F849I, F880Y, S633P, P266L, N748D, N748Q, Q758C and R756M. Some of these mutant polymerases have DNA polymerase activity, for example as conferred by mutations corresponding to Y639F and S641A of SEQ ID NO:1. Such mutant polymerases can be used for DNA sequencing by methods known in the art.

Also provided herein are mutant polymerases having greater resistance to 30 mM NaCl, 7.5 mM phosphate, 7.5 mM pyrophosphate, or 20 µg/ml single stranded DNA than a wild-type T7 RNA polymerase having SEQ ID NO:1 or a wild-type T3 RNA polymerase having SEQ ID NO:3. See Example 1. These mutant polymerases could have resistance to all of 30 mM NaCl, 7.5 mM phosphate, 7.5 mM pyrophosphate, and 20 µg/ml single stranded DNA (as T7Δ8 does) or to any one, two or three of these reagents. In some of these embodiments, the mutant polymerase has greater resistance to 30 mM NaCl than a wild-type T7 RNA polymerase having SEQ ID NO:1 or a wild-type T3 RNA polymerase having SEQ ID NO:3. In other embodiments, the mutant polymerase has greater resistance to 7.5 mM phosphate than a wild-type T7 RNA polymerase having SEQ ID NO:1 or a wild-type T3 RNA polymerase having SEQ ID NO:3. In additional embodiments, the mutant polymerase has greater resistance to pyrophosphate than a wild-type T7 RNA polymerase having SEQ ID NO:1 or a wild-type T3 RNA polymerase having SEQ ID NO:3. In still other embodiments, the mutant polymerase has greater resistance to 20 µg/ml ssDNA than a wild-type T7 RNA polymerase having SEQ ID NO:1 or a wild-type T3 RNA polymerase having SEQ ID NO:3.

The present invention is also directed to nucleic acids comprising a nucleotide sequence encoding any of the above-described mutant polymerases, i.e., a gene encoding the mutant polymerase. The nucleotide sequence can comprise any portion of a naturally occurring nucleotide sequence (e.g., the sequence of T7 or T3 RNA polymerase as encoded in the naturally occurring T7 or T3 bacteriophage, as provided in Genbank accessions M38308.1 and X02981.1, respectively, or the sequence of any of the enzymes in Table 1). Due to the redundancy in the various codons that code for specific amino acids, the nucleic acids that encode for the mutant polymerases can be comprised of substantially or even entirely a non-naturally occurring sequence. The nucleic acids comprising the nucleotide sequence can be DNA, RNA or analogs thereof. Examples of nucleic acid analogs include peptide nucleic acids, morpholino or locked nucleic acids, glycol nucleic acids or threose nucleic acids, as they are known in the art.

The above nucleic acids comprising a nucleotide sequence encoding the mutant polymerases can be combined with other nucleic acids, e.g., promoters, enhancers, antibiotic resistance genes etc. using well known methods of molecular biology. In some aspects, these combinations of nucleic acids form a vector that allows the above-described genes for the mutant polymerase to be transferred to a living cell, where the gene replicates in the cell. Thus, vectors are provided that comprise nucleic acids comprising a gene for any of the above-described mutant polymerases. The vectors can be any type known in the art, including but not limited to plasmid vectors, viral vectors, cloning vectors, shuttle vectors, or expression vectors.

Expression vectors are defined herein as DNA sequences that are required for the transcription of cloned copies of the mutant polymerase gene and the translation of its mRNA in an appropriate host.

Thus, DNA encoding the mutant polymerases may be subcloned into an expression vector for expression in a recombinant host cell. Recombinant host cells may be prokaryotic or eukaryotic, including but not limited to bacteria such as *E. coli*, plant cells, fungal cells such as yeast, mammalian cells including but not limited to cell lines of human, bovine, porcine, monkey and rodent origin, and insect cells including but not limited to *Drosophila* and silkworm derived cell lines as they are known in the art.

The expression vector may be introduced into host cells via any one of a number of techniques including but not limited to transformation, transfection, protoplast fusion, lipofection, and electroporation. The expression vector-containing cells are clonally propagated and individually analyzed to determine whether they produce the mutant polymerase protein.

Mutant polymerase-expressing host cell clones may be identified by any of several known means, including but not limited to immunological reactivity with anti-polymerase antibodies, or the presence of host cell-associated polymerase activity. Host cells transformed with any of the above-identified vectors are thus further provided herein. These host cells can be of any origin, including bacterial, archaeal, plant, fungal, insect or mammalian origin.

These mutant RNA polymerases can be used in any methods where such polymerases are used, including but not limited to synthesizing RNA probes, sequencing (particularly using the mutant polymerases that have DNA polymerase activity, as described above), and amplifying mRNA. The mutant polymerases that are resistant to phosphate, pyrophosphate, dsDNA, and/or NaCl are particularly useful for the latter methods, since inhibition of wild-type RNA polymerases by those reagents can be a concern in RNA amplification.

Thus, in additional embodiments, methods of amplifying mRNA are provided.

In additional embodiments, methods of amplifying mRNA are provided. The methods comprise (a) combine the mRNA with a reverse transcriptase and an appropriate first buffer and first reagents to form a first mixture and incubate the first mixture under conditions and for a time sufficient to synthesize a first strand of a cDNA; (b) form a second mixture by adding (i) DNA polymerase or an RNA polymerase having DNA polymerase activity and (ii) an appropriate second buffer and second reagents to the first mixture comprising the first strand cDNA, and incubating the second mixture under conditions and for a time sufficient to synthesize a second strand of the cDNA and form a double stranded cDNA (ds-cDNA); and (c) form a third mixture by adding an appropriate third buffer, third reagents and any of the mutant polymerases described herein to the second mixture comprising the ds-cDNA, and incubating the third mixture under conditions and for a time sufficient to synthesize a needed amount of amplified RNA.

In some of these embodiments, the first reagents comprise an oligo(dT)-T7 promoter, dATP, dCTP, dTTP, dGTP, and RNase inhibitor, the second reagents comprise RNase, and the third reagents comprise ATP, GTP, CTP, UTP and RNase inhibitor. In other of these embodiments, the second mixture is heat treated after the ds-cDNA is formed to denature the enzymes present therein. In some aspects, the mixture of step (c) further comprises pyrophosphatase. In other aspects, the mixture of step (c) further comprises a labeled nucleotide. In additional aspects, the mixture of step (c) further comprises pyrophosphatase and a labeled nucleotide.

The mutant polymerase of these embodiments can be any of the mutant polymerases described above, for example a mutant polymerase comprising the amino acid sequence of SEQ ID NO:2.

In various aspects of these embodiments, the DNA polymerase or RNA polymerase having DNA polymerase activity of step (b) is the mutant polymerase described above that has DNA polymerase activity (e.g., the mutant polymerase having mutations corresponding to Y639F and S641A of SEQ ID NO:2).

These methods are particularly useful where the cDNA is not purified before step (c) and where the method is performed in one container without removal of any mixture before the amplified RNA is synthesized, since the mutant polymerases described herein are resistant to reagents that are generally present in concentrations that are inhibitory to wild-type RNA polymerases.

In further embodiments, a composition is provided. The composition comprises any of the mutant polymerases described herein, and a reagent at a concentration that is inhibitory to wild-type T7 RNA polymerase. In these compositions, the reagent is a salt, phosphate, pyrophosphate or single stranded DNA. In some aspects, the reagent is a salt, for example NaCl, KCl, or any other salt that may be present in such a composition, where the salt is inhibitory to wild-type T7 RNA polymerase. The salt can be at any inhibitory concentration, for example 10 mM, 20 mM, 30 mM, any concentration between these concentrations, or any concentration above 30 mM. In other aspects, the reagent is phosphate or pyrophosphate, for example at 1 mM, 2 mM, 5 mM, 10 mM, any concentration between these concentrations, or any concentration above 10 mM. In further aspects the reagent is ssDNA, for example at 5 µg/ml, 10 µg/ml, 15 µg/ml, 20 µg/ml, any concentration between these concentrations, or any concentration above 20 µg/ml.

The mutant polymerase of these compositions can be any of the mutant polymerases described above, for example a mutant polymerase comprising the amino acid sequence of SEQ ID NO:2.

In some of these embodiments, the composition comprises a cDNA and reagents appropriate to transcribe the cDNA into RNA. For example the composition can be the mixture of step (c) in the methods of amplifying RNA described above.

In other of these embodiments, the composition is in a kit, where the mutant polymerase and reagent are in separate containers or the same container as appropriate. In some of these kits, the kit further comprises reagents, buffers and/or enzymes for amplifying mRNA by the method described above. For example, such kits, may comprise a reverse transcriptase and/or a DNA polymerase, and/or, e.g., any combination of an oligo(dT)-T7 promoter, dATP, dCTP, dTTP, dGTP, an RNase inhibitor, RNase, ATP, GTP, CTP, and/or UTP. Again, these reagents can be in separate containers or mixed together in any combination of containers. Instructions as appropriate may also be included in these kits.

Preferred embodiments are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

EXAMPLE 1

Isolation and Characterization of a T7 RNA Polymerase that is Resistant to Phosphate The T7 RNA polymerase gene was fused to a histidine tag for ease of purification as described by Ellinger and Ehricht (1998), in the expression vector pQE30 (Qiagen). This plasmid, pQE30-T7, was used for all subsequent modifications.

Mutations were generated in the plasmid pQE30-T7 using PCR generated mutations. The following primers were used to amplify pQE30-T7 and generate mutations:

```
                                             (SEQ ID NO: 4)
F-T7d  pGTAGGGCACGTCTACAAGAAAG
       binds pQE30-T7 at bases 667-688.

(SEQ ID NO: 5)
R-T7d  pGTTGAGTTGTTCCTCAACGTTTTTC
       binds pQE30-T7 at 636-660.
```

The mutagenic amplification was performed using the following mixture:
10 ng pQE30-T7
160 nM F-T7d
160 nM R-T7d
200 µM each of dATP, dCTP200, dGTP and TTP
2.5 units PfuUltra Hotstart DNA Polymerase
PfuUltra buffer, supplied by the manufacturer (Stratagene, La Jolla, Calif.).

This mixture was heated to 94° C. for two minutes then cycled 15 times using a cycle of 94° C. 20 seconds, 55.2° C.

20 seconds, 72° C. 6 minutes 10 seconds. This was followed by an extension at 72° C. for 5 minutes. After synthesis, starting template was removed by digestion with the restriction endonuclease DpnI (New England Biolabs, Ipswich, Mass.), which cleaves only the methylated starting DNA. The resulting DNA was separated by agarose gel (0.7%) followed by purification from the gel using the Qiagen QiaQuick gel extraction kit (Qiagen, Valencia, Calif.). The purified DNA was ligated using Quick Ligase (New England BioLabs, Ipswich, Mass.) as recommended by the manufacturer. The ligated DNA was used to transform the Escherichia coli strain Top10F' (Life Technologies, Carlsbad, Calif.). Several colonies grew on LB plates (Davis et al., 1980) containing 100 µg/ml ampicillin. Individual colonies were isolated, and the DNA was isolated from those colonies using standard techniques (Sambrook and Russell, 2001). Agarose gel electrophoresis was used to identify plasmids with large deletions that are unlikely to express active T7 RNA polymerase.

Strains containing the correct size plasmid were grown and induced in small cultures, and the modified T7 RNA Polymerases were purified using small Nickel-NTA columns (Qiagen, Valencia, Calif.) using standard techniques (Elinger and Ehricht, 1998). One mutation was chosen for further study.

Determining the Sequence of the Altered T7 RNA Polymerase.

The entire gene for the T7 RNA Polymerase that was chosen for further study was sequenced. Only a single mutation was found, a deletion of 24 base pairs, causing a deletion of 8 amino acid residues in the protein. References to peptide sequence of T7 RNA polymerase follow the numbering of amino acids residues as described by Dunn and Studier (1981) and Stahl and Zinn (1981) and as provided in SEQ ID NO:1. The amino acid residues missing in the enhanced T7 RNA polymerase described above are residues 167 to 174. This is adjacent to a region known to be involved in transcription termination. The sequence that is deleted in the modified T7 RNA polymerase is EEQLNKRV (SEQ ID NO:6).

Standard Transcription Assay.

The plasmid transcription template used in this work is pTAN, a plasmid containing a neomycin resistance gene after a T7 promoter that is linearized using the restriction enzyme PvuII. The run-off transcript that is produced from this plasmid is 790 bases long. The transcription reactions described herein contain
Template DNA (varying amounts)
80 mM Tris-HCl, pH 7.9
10 mM DTT
12 mM MgCl$_2$
1.5 mM Spermidine
10 mM NaCl
200 µg/ml BSA
3.75 mM each of UTP, ATP, CTP and GTP
2000 u/ml RNase Inhibitor (2000 units/ml)
12 u/ml Pyrophosphatase
T7 RNA Polymerase (amount varies).
If labeled nucleotides are used, the modified nucleotide replaces one fourth of the cognate nucleotide.

The reactions are assembled at room temperature then incubated at 37° C. for various times. Reactions are stopped by the addition of EDTA to 20 mM.

Quantifying a Single Transcription Product.

To determine the relative yield of a transcription reaction, the products of the transcription reactions were separated using a 1.2% Lonza flash gel (Lonza, Basel, Switzerland) as recommended. The gel was photographed using a Kodak 440 image scanner and a 523 nm cut-off filter. RNA specific bands were outlined using the manual region of interest (ROI) function in the Kodak Molecular Imaging software (version 4.04). The same size ROI was used for each band and a control area with no RNA was used as background. The NET intensity is calculated as the intensity of the RNA band with the background intensity subtracted. The intensity values were compared on a single gel, but not between gels.

Determining the Effect of Excess Single-Stranded DNA on Transcription Using the Modified T7 RNA Polymerase.

The inventors desired a novel RNA polymerase that would be resistant to excess single-stranded DNA, as commonly occurs in many molecular biology techniques (VanGelder et al., 1990). Table 2 shows the relative amount of specific product produced in a standard transcription reaction using 1.25 µg/ml plasmid template, and 100 units per ml T7 RNA polymerase in a 20 µl reaction at 37° C. for 18 hours. Single-stranded Salmon sperm DNA was used to test the sensitivity of T7 RNA polymerase to ssDNA.

TABLE 2

Relative transcription activity of wild-type T7 polymerase with the mutant polymerase T7Δ8 in the presence or absence of 20 µg/ml single stranded DNA

| Polymerase | excess DNA | Relative Activity |
|---|---|---|
| wild-type T7 | no | 100% |
| wild-type T7 | 20 µg/ml | 71% |
| T7 Δ8 | no | 100% |
| T7 Δ8 | 20 µg/ml | 172% |

With wild-type T7 RNA polymerase, the ssDNA inhibited synthesis of the template specific product. The mutant T7 RNA polymerase, T7Δ8, appeared to be stimulated in the presence of ssDNA.

Determining the Effect of Excess Phosphate or Pyrophosphate on Transcription Using the Modified T7 RNA Polymerase.

During transcription, as the RNA chain is elongated, pyrophosphate is produced. Pyrophosphate is broken down into phosphate by either endogenous enzymes, chemical reactions or by the addition of pyrophosphatase (Cunningham and Olfengand 1990). Phosphate can inhibit the transcription reaction, so the T7Δ8 mutant was tested for inhibition by phosphate. Table 3 shows the relative amount of specific product produced in a standard transcription reaction using 1.25 µg/ml plasmid template, and 100 units per ml enzyme in a 20 µl reaction at 37° C. for 18 hours. The phosphate or pyrophosphate was added in the form of a sodium salt at pH 8.0.

TABLE 3

Relative transcription activity of wild-type T7 polymerase and polymerase T7Δ8 in the presence or absence of 7.5 mM pyrophosphate or phosphate

| Polymerase | no addition | 7.5 mM pyrophosphate | 7.5 mM phosphate |
|---|---|---|---|
| Wild-type T7 | 100% | 71% | 73% |
| T7Δ8 | 100% | 139% | 204% |

With wild-type T7 RNA polymerase, the excess phosphate or pyrophosphate inhibited synthesis of the template specific product. The mutant T7 RNA polymerase, T7Δ8, appeared to be stimulated in the presence of excess phosphate. The stimulation by pyrophosphate may be due to contaminating phosphate in the pyrophosphate preparation due to breakdown of the pyrophosphate into phosphate.

FIG. 2 shows the relative amount of specific product produced in a standard transcription reaction using 0.625 μg/ml plasmid template, and 100 units per ml enzyme in a 20 μl reaction at 37° C. for 18 hours in the standard buffer with various concentrations of potassium phosphate added. The mutant T7 RNA polymerase was stimulated by phosphate up to about 5 mM, while the unmodified enzyme was inhibited by all phosphate concentrations tested.

Table 4 shows the relative amount of specific product produced in a standard transcription reaction using 2 μg/ml plasmid template and 500 units per ml enzyme at 37° C. for 18 hours in the standard buffer with various concentrations of potassium phosphate or pyrophosphate added.

TABLE 4

Relative transcription activity of wild type T7 polymerase and polymerase T7Δ8 in the presence or absence of varying concentrations of pyrophosphate or phosphate

|  | Wild-Type | T7Δ8 |
|---|---|---|
| 0 mM Pi | 1.00 | 1.00 |
| 10 mM Pi | 0.47 | 0.69 |
| 5 mM Pi | 0.69 | 1.03 |
| 20 mM PPi | 0.16 | 0.16 |
| 10 mM PPi | 0.52 | 0.52 |
| 5 mM PPi | 0.78 | 1.16 |

Determining the Effect of High Salt (NaCl) on Transcription Using the Modified T7 RNA Polymerase.

Figure 3:
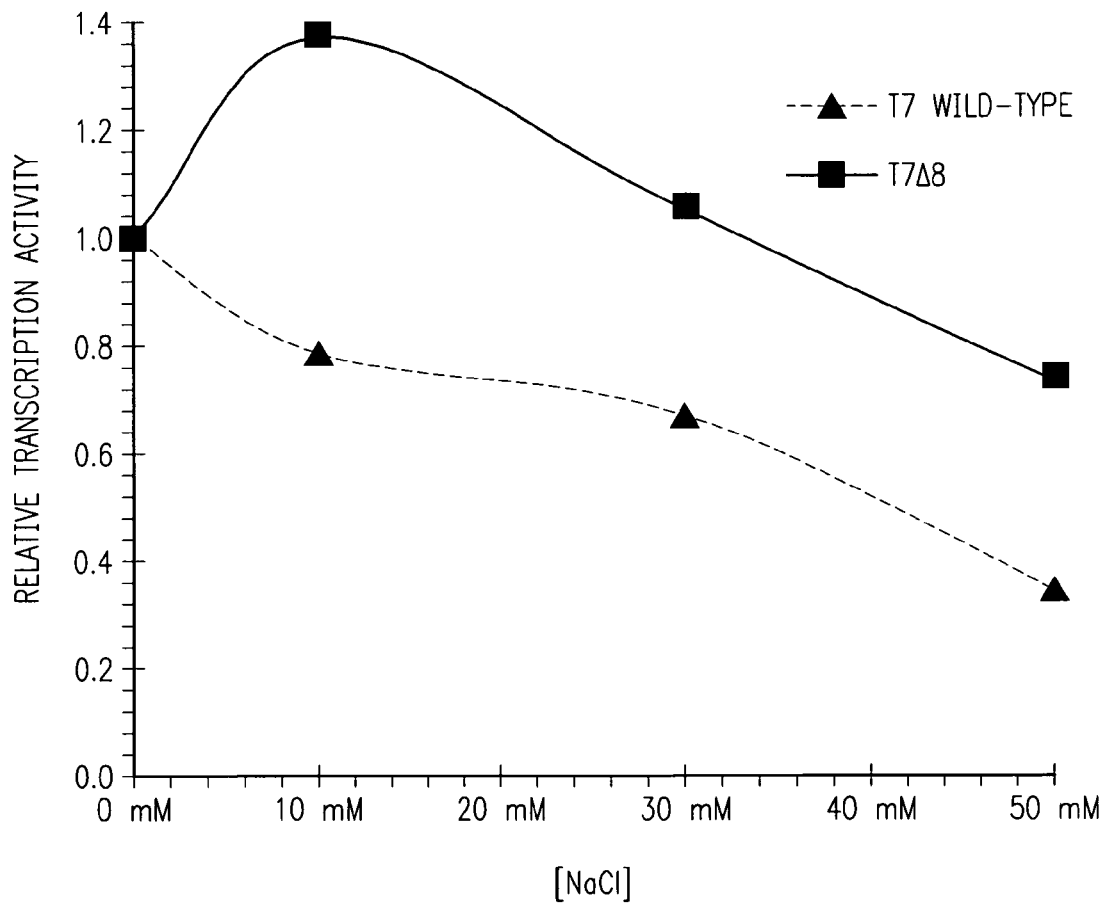
FIG. 3 is a graph comparing relative transcription activity of wild-type T7 polymerase with the mutant polymerase T7Δ8 in the presence of varying concentrations of NaCl.

High salt concentrations are known to inhibit transcription from many bacteriophage RNA polymerases, such as T7, SP6 and T3 (Milburn et al., 1993, Milburn et al. 2003). T7Δ8 was compared with wild-type T7. FIG. 3 shows the relative amount of specific product produced in a standard transcription reaction using 1.25 μg/ml plasmid template, and 200 units per ml enzyme in a 20 μl reaction at 37° C. for 18 hours in the standard buffer without added NaCl or with increasing concentrations of NaCl.

As shown in FIG. 3, with wild-type T7 RNA polymerase, the excess NaCl inhibited synthesis of the template specific product. The mutant T7 RNA polymerase, T7Δ8, is not inhibited in the presence of 10 mM NaCl, and is generally less affected by salt.

EXAMPLE 2

Use of T7Δ8 for One Tube RNA Amplification Reactions

The mutant T7 polymerase described in Example 1 (T7Δ8) was compared with wild-type T7 (SEQ ID NO:1) in RNA amplification reactions performed in a single tube as follows.
First Strand Synthesis—5 μl
100 ng human reference RNA (Stratagene, La Jolla, Calif.)
2.5 μM T7T24 primer
2 mM each of dTTP, dCTP, dATP and dGTP
First Strand buffer: 50 mM Tris-HCl, pH 8.3, 75 mM KCl, 3 mM MgCl$_2$, and 5 mM DTT
100 units reverse transcriptase
100 units RNase Inhibitor
The above mixture was incubated at 42° C. for 2 h.
Second Strand Synthesis
After the first strand synthesis incubation, the following was added to the mixture to 25 potassium phosphate buffer, pH 7.0 to 20 mM
DNA Polymerase I (9 units)
RNase H (20 units)
This mixture was incubated at 16° C. for 2 h
After the second strand synthesis incubation, the enzymes were denatured by incubation at 65° C. for 10 min.
Transcription
Following the above steps, the following was added to the mixture to 75 μl:
7.5 μl 10× transcription buffer consisting of 800 mM Tris-HCl pH 7.9, 120 mM MgCl$_2$, 15 mM Spermidine, 100 mM NaCl, and 2 mg/ml BSA
7.5 μl 100 mM DTT
7.5 μl of a mixture of 37.5 mM ATP, 37.5 mM GTP, 25 mM CTP, 25 mM UTP, 12.5 mM Bio-11-CTP and 12.5 mM Bio-16-UTP
150 units Porcine RNase Inhibitor
0.9 units pyrophosphatase
250 units of wild type T7 RNA polymerase or 1250 units of T7Δ8
The reaction proceeded at 37° for 16 hours.
After transcription, the RNA produced was purified using Qiagen RNeasy mini columns.

The results of these studies are provided in Table 5. The standard deviations (SD) are based on two replications. As shown in Table 5, T7Δ8 provided an aRNA yield that compared favorably to wild-type T7.

TABLE 5

Yield of amplified RNA ("aRNA") prepared using wild-type T7 polymerase (WT) and polymerase T7Δ8 (Mut) in a one tube amplification method

| Sample | μg aRNA | SD |
|---|---|---|
| Set 1 WT | 21.2 | 0.5 |
| Set 1 Mut | 43.5 | 1.2 |
| Set 2 WT | 15.7 | 0.9 |
| Set 2 Mut | 31.3 | 0.3 |

Wild-type T7 and T7Δ8 were also compared for their ability to amplify RNA for use on arrays. The RNA amplification materials and procedures were as follows.
First Strand Synthesis—5 μl
100 ng human reference RNA, human colon RNA, or human thymus RNA
2.5 μM T7T24 primer
1 mM each of dTTP, dCTP, dATP and dGTP
First Strand buffer: 50 mM Tris-HCl, pH 8.3, 75 mM KCl, 3 mM MgCl$_2$, and 5 mM DTT
100 units reverse transcriptase
100 units RNase inhibitor
The above mixture was incubated at 42° C. for 2 h.
Second Strand Synthesis
After the first strand synthesis incubation, the following was added to the mixture to 25 μl: potassium phosphate buffer, pH 7.0 to 40 mM
MgCl$_2$ to 1 mM
DNA polymerase (9 units)
RNase H (20 units)
This mixture was incubated at 16° C. for 2 h
After the second strand synthesis incubation, the enzymes were denatured by incubation at 65° C. for 10 min.
Transcription
Following the above steps, the following was added to the mixture to 75 μl:
7.5 μl 10× transcription buffer consisting of 800 mM Tris-HCl pH 7.9, 120 mM MgCl$_2$, 15 mM spermidine, 100 mM NaCl, and 2 mg/ml BSA 7.5 µl 100 mM DTT
7.5 µl of a mixture of 37.5 mM ATP, 37.5 mM GTP, 25 mM CTP, 25 mM UTP, 12.5 mM Bio-11-CTP and 12.5 mM Bio-16-UTP
150 units porcine RNase inhibitor
0.9 units pyrophosphatase
250 units wild type T7 RNA polymerase or 1250 units of T7Δ8

The reaction proceeded at 37° for 16 hours.

After transcription, the RNA produced was purified using Qiagen RNeasy mini columns. The purified RNAs were applied to Affymetrix HG-U133a chips according to the manufacturer's protocols.

The results for the human reference RNA is provided in Table 6; the thymus and colon results are provided in Table 7.

TABLE 6

Comparison of expression data from human reference RNA amplified by wild-type T7 and T7Δ8

| Human Reference RNA | WT | T7Δ8 |
|---|---|---|
| % P | 51.6 | 51.5 |
| % M | 1.9 | 1.9 |
| GAPDH 3'/5' | 0.98 | 1.01 |
| GAPDH 3'/M | 1.06 | 1.13 |
| Actin 3'/5' | 1.93 | 1.94 |
| Actin 3'/M | 1.12 | 0.82 |
| Scale Factor | 0.97 | 1.08 |
| $R^2 = 0.977$ | | |

TABLE 7

Comparison of expression data from (a) human thymus RNA and (b) human colon RNA amplified by wild-type T7 and T7Δ8*

| | (a) | | | (b) | |
|---|---|---|---|---|---|
| Chip ID | WT T7 thymus 10 µg ECT5 | T7Δ8 thymus 10 µg EMT6 | Chip ID | WT T7 colon 7 µg ECC3 | T7Δ8 colon 7 µg EMC4 |
| % P | 44.3 | 42.3 | % P | 42.7 | 44.3 |
| % A | 53.8 | 56 | % A | 55.3 | 53.8 |
| % M | 1.9 | 1.7 | % M | 1.9 | 1.9 |
| Scale factor | 2.283 | 2.62 | Scale factor | 3.34 | 3.47 |
| Actin 3'/5' | 2.22 | 3.08 | Actin 3'/5' | 9.69 | 5.96 |
| Actin 3'/M | 1.34 | 1.11 | Actin 3'/M | 2.6 | 1.51 |
| GAPDH 3'/5' | 1.17 | 1.22 | GAPDH 3'/5' | 2.92 | 2.61 |
| GAPDH 3'/M | 1.27 | 1.15 | GAPDH 3'/M | 2.28 | 2 |
| $RSQ_{staining}$ | 0.996 | 0.994 | $RSQ_{staining}$ | 0.987 | 0.992 |
| | $R^2 = 0.983$ | | | $R^2 = 0.979$ | |

*% P = percentage of probe sets deemed present in the RNA; % A = percentage of probe sets deemed absent in the RNA; % M = percentage of probe sets deemed marginally present; Scale factor = number that the signal is multiplied by to make the average value the same for all chips; RSQstaining is a measure of the evenness of the staining on the chip; the Actin and GAPDH measurements are relative amounts of these housekeeping genes present, using different probes as indicated; The $R^2$ values compare mutant to wild-type on the same RNA. Further information can be obtained in "GeneChip ® Expression Analysis" available at www.affymetrix.com.

As shown in Tables 6 and 7, the results using RNA amplified by wild-type T7 was very similar to the results using RNA amplified by T7Δ8, establishing that T7Δ8 can be substituted for wild-type T7 polymerase in procedures to produce high quality amplified RNA.

REFERENCES

Altschul, S F, Madden, T L, Schäffer, A A, Zhang, J, Zhang, Z, Miller, W, and Lipman D J (1997) "Gapped BLAST and PSI-BLAST: a new generation of protein database search programs." Nucleic Acids Res. 25:3389-3402.

Altschul, S F, Wootton, J C, Gertz, E M, Agarwala, R, Morgulis, A, Schäffer, A A, and Yu, Y-K (2005) "Protein database searches using compositionally adjusted substitution matrices." FEBS J. 272:5101-5109.

Brieba, L. G. and Sousa, R. (2000) "Roles of Histidine 784 and Tyrosine 639 in Ribose Discrimination by T7 RNA Polymerase." Biochemistry 39: 919-923.

Chelliserrykattil, J, Cai, G., and Ellington, A D (2001) "A combined in vitro/in vivo selection for polymerases with novel promoter specificities." BMC Biotechnology 1:13.

Cunningham P. R., Ofengand J. (1990) "Use of inorganic pyrophosphatase to improve the yield of in vitro transcription reactions catalyzed by T7 RNA polymerase." Biotechniques. 9:713-4.

Davis, R. W., Botstein, D. and Roth, J. R. (1980) A Manual for Genetic Engineering: Advanced Bacterial Genetics. (Cold Spring Harbor Laboratory Press, Cold Spring Harbor, N.Y.).

Dunn, J. J. and Studier, F. W. J. (1981) "Nucleotide sequence from the genetic left end of bacteriophage T7 DNA to the beginning of gene 4." J. Mol. Biol. 148:303-330.

Ellinger, T. and Ehricht, R. (1998). "Single-Step Purification of T7 RNA Polymerase with a 6-Histidine Tag." Biotechniques 24:718-720.

He, B. (1996) "A gene expression system based on bacteriophage RNA polymerases and characterization of bacteriophage T7 RNA polymerase. Thesis/Dissertation, State University of New York, Health Science Center at Brooklyn, Brooklyn N.Y.

Izawa, M., Sasaki, N., Watahiki, M., Ohara, E., Yoneda, Y., Murimatsu, M., Okazaki, Y. and Hayashizaki, Y. (1998) "Recognition Sites of 3'-OH Group by T7 RNA Polymerase and Its Application to Transcriptional Sequencing." J. Biol. Chem. 273: 14242-14246.

Joyce, C. M. (1997) "Choosing the Right Sugar: How Polymerases Select a Nucleotide Substrate." Proc Natl. Acad. Sci. USA 94: 1619-1622.

Kostyuk, D. A., Dragan, S. M., Lyakhov, D. L., Rechinsky, V. O., Tunitskaya, V. L., Chernov, B. K. and Kochetkov, S. N. (1995) "Mutants of T7 RNA Polymerase that are able to Synthesize Both RNA and DNA." FEBS Letters 369:165-168.

Lyakhov, D. L., Ilgenfrits, H., Chernov, B. K., Dragon, S. M., Rechinsky, V. O., Pokholok, D. K., Tunitskaya, V. L. and Kochetkov, S. N. (1992) "Site-Specific Mutagenesis of the Lys-172 Residue in Phage T7 RNA Polymerase: Characterization of the Transcriptional Properties of the Mutant Proteins." Mol. Biol. 26: 679-687.

Lyakhov, D. L., He, B., Zhang, X., Studier, F. W., Dunn, J. J. and McAllister, W. T. (1997) "Mutant Bacteriophage T7 RNA polymerases with Altered Termination Properties." J. Mol. Biol. 269: 28-40.

Macdonald, L E, Zhou, Y. and McAllister, W T (1993) "Characterization of two types of termination signal for bacteriophage T7 RNA polymerase." J. Mol. Biol. 238:145-158.

McAllister, W. T., Kurkarin, A. (2006) "Methods and Materials for Reducing Production of Aberrant Products During RNA Synthesis." Patent Application US 2006/0063154 A1

Padilla, R. and Sousa, R. (2002) "A Y689F/H784A T7 RNA Polymerase Double Mutant Displays Superior Properties for Synthesizing RNAs with Non-Canonical NTPs." Nucleic Acids Res. 30:e138.

Sambrook, J. and Russell, D. W. (2001) Molecular Cloning: A Laboratory Manual. (Cold Spring Harbor Laboratory Press, Cold Spring Harbor, N.Y.).

Stahl, S. J. and Zinn, K. (1981) "Nucleotide sequence of the cloned gene for bacteriophage T7 RNA polymerase." J. Mol. Biol. 148:481-485.

Tunitskaya, V. L. and Kochetkov, S. N. (2002) "Structural-Functional Analysis of Bacteriophage T7 RNA Polymerase." Biochemistry (Moskow) 67: 1124-1135.

Van Gelder, R. N., vonZastrow. M. E., Yool, A., Dement, W. C., Barchas, J, D., Eberwine, J. H. (1990) "Amplified RNA synthesized from limited quantities of heterogeneous cDNA." Proc Natl Acad Sci USA 87:1663-1667.

Wang, E., Miller, L D, Ohnmacht, G. A., Liu, E. T., and Marincola, F. M. (2000) "High-fidelity mRNA amplification for gene profiling." Nat. Biotechnol. 18:457-459.

Yang, X-M and Richardson C C (1997) "Amino acid changes in a unique sequence of bacteriophage T7 DNA polymerase alter the processivity of nucleotide polymerization." J. Biol. Chem. 272:6599-6606.

European Patent Application No. EP1403364A1
U.S. Pat. No. 5,256,555.
U.S. Pat. No. 5,385,834.
U.S. Pat. No. 6,586,218.
U.S. Pat. No. 6,586,219.
U.S. Pat. No. 7,335,471.
U.S. Pat. No. 7,507,567.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

APPENDIX

SEQ ID NOs

SEQ ID NO: 1 -
Wild type T7 RNA Polymerase - Genbank Accession NP041960.1
Residues deleted in SEQ ID NO: 2 - 167-174 - in bold underline

```
  1    mntiniaknd  fsdielaaip  fntladhyge  rlareqlale  hesyemgear  frkmferqlk 61    agevadnaaa  kplittllpk  miarindwfe  evkakrgkrp  tafqflqeik  peavayitik 121    ttlacltsad  nttvqavasa  igraiedear  fgrirdleak  hfkknveeql  nkrvghvykk 181    afmqvveadm  lskgllggea  wsswhkedsi  hvgvrcieml  iestgmvslh  rqnagvvgqd 241    setielapey  aeaiatraga  lagispmfqp  cvvppkpwtg  itgggywang  rrplalvrth 301    skkalmryed  vympevykai  niaqntawki  nkkvlavanv  itkwkhcpve  dipaiereel 361    pmkpedidmn  pealtawkra  aaavyrkdka  rksrrislef  mleqankfan  hkaiwfpynm 421    dwrgrvyavs  mfnpqgndmt  kglltlakgk  pigkegyywl  kihgancagv  dkvpfperik 481    fieenhenim  acaksplent  wwaeqdspfc  flafcfeyag  vqhhglsync  slplafdgsc 541    sgiqhfsaml  rdevggravn  llpsetvqdi  ygivakkvne  ilqadaingt  dnevvtvtde 601    ntgeisekvk  lgtkalagqw  laygvtrsvt  krsvmtlayg  skefgfrqqv  ledtiqpaid 661    sgkglmftqp  nqaagymakl  iwesvsvtvv  aaveamnwlk  saakllaaev  kdkktgeilr 721    krcavhwvtp  dgfpvwqeyk  kpiqtrinlm  flgqfrlqpt  intnkdseid  ahkqesgiap 781    nfvhsqdgsh  lrktvvwahe  kygiesfali  hdsfgtipad  aanlfkavre  tmvdtyescd 841    vladfydqfa  dqlhesqldk  mpalpakgnl  nlrdilesdf  afa
```

SEQ ID NO: 2 -
Mutant T7Δ8

```
  1    mntiniaknd  fsdielaaip  fntladhyge  rlareqlale  hesyemgear  frkmferqlk 61    agevadnaaa  kplittllpk  miarindwfe  evkakrgkrp  tafqflqeik  peavayitik 121    ttlacltsad  nttvqavasa  igraiedear  fgrirdleak  hfkknvghvykk 173    afmqvveadm  lskgllggea  wsswhkedsi  hvgvrcieml  iestgmvslh  rqnagvvgqd 233    setielapey  aeaiatraga  lagispmfqp  cvvppkpwtg  itgggywang  rrplalvrth 293    skkalmryed  vympevykai  niaqntawki  nkkvlavanv  itkwkhcpve  dipaiereel 353    pmkpedidmn  pealtawkra  aaavyrkdka  rksrrislef  mleqankfan  hkaiwfpynm 413    dwrgrvyavs  mfnpqgndmt  kglltlakgk  pigkegyywl  kihgancagv  dkvpfperik
```

APPENDIX-continued

SEQ ID NOs

```
463   fieenhenim acaksplent wwaeqdspfc flafcfeyag vqhhglsync slplafdgsc
533   sgiqhfsaml rdevggravn llpsetvqdi ygivakkvne ilqadaingt dnevvtvtde
593   ntgeisekvk lgtkalagqw laygvtrsvt krsvmtlayg skefgfrqqv ledtiqpaid
653   sgkglmftqp nqaagymakl iwesysvtvv aaveamnwlk saakllaaev kdkktgeilr
713   krcavhwvtp dgfpvwqeyk kpiqtrlnlm flgqfrlqpt intnkdseid ahkqesgiap
773   nfvhsqdgsh lrktvvwahe kygiesfali hdsfgtipad aanlfkavre tmvdtyescd
833   vladfydqfa dqlhesqldk mpalpakgnl nlrdilesdf afa
```

SEQ ID NO: 3 -
Wild type T3 RNA Polymerase - Genbank Accession NP523301.1
Residues 168-175, corresponding to deleted residues in SEQ ID NO: 2,
in bold underline

```
  1   mniieniekn dfseielaai pfntladhyg salakeqlal ehesyelger rflkmlerqa
 61   kageiadnaa akpllatllp klttrivewl eeyaskkgrk psayaplqll kpeasafitl
121   kvilasltst nmttiqaaag mlgkaiedea rfgrirdlea khfkkhveeq lnkrhgqvyk
181   kafmqvvead migrgllgge awsswdkett mhvgirliem liestglvel qrhnagnags
241   dhealqlaqe yvdvlakrag alagispmfq pcvvppkpwv aitgggywan grrplalvrt
301   hskkglmrye dvympevyka vnlaqntawk inkkvlavvn eivnwkncpv adipslerqe
361   lppkpddidt neaalkewkk aaagiyrldk arvsrrisle fmleqankfa skkaiwfpyn
421   mdwrgrvyav pmfnpqgndm tkglltlakg kpigeegfyw lkihgancag vdkvpfperi
481   afiekhvddi lacakdpinn twwaeqdspf cflafcfeya gvthhglsyn cslplafdgs
541   csgiqhfsam lrdevggrav nllpsetvqd iygivaqkvn eilkqdaing tpnemitvtd
601   kdtgeisekl klgtstlaqq wlaygvtrsv tkrsvmtlay gskefgfrqq vlddtiqpai
661   dsgkglmftq pnqaagymak liwdaysvtv vaaveamnwl ksaakllaae vkdkktkeil
721   rhrcavhwtt pdgfpvwqey rkplqkrldm iflgqfrlqp tintlkdsgi dahkqesgia
781   pnfvhsqdgs hlrmtvvyah ekygiesfal ihdsfgtipa dagklfkavr etmvityenn
841   dvladfysqf adqlhetqld kmpplpkkgn lnlqdilksd fafa
```

SEQ ID NO: 4 -
Forward primer F-T7
GTAGGGCACGTCTACAAGAAAG

SEQ ID NO: 5 -
Reverse primer R-T7
GTTGAGTTGTTCCTCAACGTTTTTC

SEQ ID NO: 6 -
Amino acid residues deleted in T7Δ8.
EEQLNKRV

---

What is claimed is:

1. A synthetically generated polymerase selected from (i) a protein having an amino acid sequence that is at least 90% homologous to the amino acid sequence of the polymerase of SEQ ID NO: 1 and a deletion of the 8 amino acids corresponding to residues 167-174 of SEQ ID NO: 1 and (ii) a protein having an amino acid sequence that is at least 90% homologous to the amino acid sequence of the polymerase of SEQ ID NO:3 and a deletion of the 8 amino acids corresponding to residues 168-175 of SEQ ID NO: 3.

2. The polymerase of claim 1, having an amino acid sequence that is at least 95% homologous to the polymerase of SEQ ID NO: 1 or the polymerase of SEQ ID NO:3.

3. The polymerase of claim 1, having an amino acid sequence that is at least 98% homologous to SEQ ID NO:1 or SEQ ID NO:3.

4. The polymerase of claim 1, having an amino acid sequence that is at least 99% homologous to SEQ ID NO:1 or SEQ ID NO:3.

5. A polymerase having the amino acid sequence of SEQ ID NO: 2.

6. The polymerase of claim 1, having greater resistance to 30 mM NaCl, 7.5 mM phosphate, 7.5 mM pyrophosphate, or 20 µg/ml single stranded DNA than the wild-type T7 RNA polymerase having the sequence of SEQ ID NO:1 or the wild-type T3 RNA polymerase having the sequence of SEQ ID NO:3.

7. The polymerase of claim 1, further comprising at least one mutation corresponding to mutations in SEQ ID NO:1 selected from the group consisting of Y639F, S641A, F644Y, F667Y, E222K, S430P, F849I, F880Y, S633P, P266L, N748D, N748Q, Q758C and R756M.

8. The polymerase of claim 7, comprising mutations corresponding to Y639F and S641A in SEQ ID NO:1.

9. The polymerase of claim 1 having greater resistance to 30 mM NaCl, 7.5 mM phosphate, or 20 µg/ml single stranded DNA than a wild-type T7 RNA polymerase having the sequence of SEQ ID NO:1 or a wild-type T3 RNA polymerase having the sequence of SEQ ID NO:3.

10. A method of amplifying mRNA comprising
  (a) combining the mRNA with a reverse transcriptase and an appropriate first buffer and first reagents to form a first mixture and incubate the first mixture under conditions and for a time sufficient to synthesize a first strand of a cDNA;
  (b) forming a second mixture by adding (i) DNA polymerase or an RNA polymerase having DNA polymerase activity and (ii) an appropriate second buffer and second reagents to the first mixture comprising the first strand cDNA, and incubating the second mixture under conditions and for a time sufficient to synthesize a second strand of the cDNA and form a double stranded cDNA (ds-cDNA); and
  (c) forming a third mixture by adding an appropriate third buffer, third reagents and the polymerase of any one of claims 1, 2, 3, 4, 5, 6, 7, 8 and 9 to the second mixture comprising the ds-cDNA, and incubating the third mixture under conditions and for a time sufficient to synthesize a needed amount of amplified RNA.

11. A composition comprising the polymerase of any one of claims 1, 2, 3, 4, 5, 6, 7, 8 and 9, and a reagent selected from a salt, phosphate, pyrophosphate or single stranded DNA at a concentration that is inhibitory to wild-type T7 RNA polymerase.

12. The composition of claim 11, wherein said composition is in a kit, and the kit further comprises one or more reagents, buffers and/or enzymes for amplifying mRNA.

* * * * *

SEQUENCE LISTING

<160> NUMBER OF SEQ ID NOS: 7

<210> SEQ ID NO 1
<211> LENGTH: 883
<212> TYPE: PRT
<213> ORGANISM: Unknown
<220> FEATURE:
<223> OTHER INFORMATION: Description of Unknown: Enterobacteria
      phage T7

<400> SEQUENCE: 1

-continued

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65              70                  75                  80

Met Ile Ala Arg Ile Asn Asp Trp Phe Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415
```

```
Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
            450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
            530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val His
770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
```

```
                    835                 840                 845

Phe Ala Asp Gln Leu His Glu Ser Gln Leu Asp Lys Met Pro Ala Leu
            850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 2
<211> LENGTH: 875
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Gly His Val Tyr Lys Lys Ala Phe Met Gln
                165                 170                 175

Val Val Glu Ala Asp Met Leu Ser Lys Gly Leu Leu Gly Gly Glu Ala
            180                 185                 190

Trp Ser Ser Trp His Lys Glu Asp Ser Ile His Val Gly Val Arg Cys
        195                 200                 205

Ile Glu Met Leu Ile Glu Ser Thr Gly Met Val Ser Leu His Arg Gln
    210                 215                 220

Asn Ala Gly Val Val Gly Gln Asp Ser Glu Thr Ile Glu Leu Ala Pro
225                 230                 235                 240

Glu Tyr Ala Glu Ala Ile Ala Thr Arg Ala Gly Ala Leu Ala Gly Ile
                245                 250                 255

Ser Pro Met Phe Gln Pro Cys Val Val Pro Pro Lys Pro Trp Thr Gly
            260                 265                 270

Ile Thr Gly Gly Gly Tyr Trp Ala Asn Gly Arg Arg Pro Leu Ala Leu
        275                 280                 285

Val Arg Thr His Ser Lys Lys Ala Leu Met Arg Tyr Glu Asp Val Tyr
    290                 295                 300

Met Pro Glu Val Tyr Lys Ala Ile Asn Ile Ala Gln Asn Thr Ala Trp
```

```
            305                 310                 315                 320
Lys Ile Asn Lys Lys Val Leu Ala Val Ala Asn Val Ile Thr Lys Trp
                325                 330                 335
Lys His Cys Pro Val Glu Asp Ile Pro Ala Ile Glu Arg Glu Glu Leu
                340                 345                 350
Pro Met Lys Pro Glu Asp Ile Asp Met Asn Pro Glu Ala Leu Thr Ala
                355                 360                 365
Trp Lys Arg Ala Ala Ala Val Tyr Arg Lys Asp Lys Ala Arg Lys
        370                 375                 380
Ser Arg Arg Ile Ser Leu Glu Phe Met Leu Glu Gln Ala Asn Lys Phe
385                 390                 395                 400
Ala Asn His Lys Ala Ile Trp Phe Pro Tyr Asn Met Asp Trp Arg Gly
                405                 410                 415
Arg Val Tyr Ala Val Ser Met Phe Asn Pro Gln Gly Asn Asp Met Thr
                420                 425                 430
Lys Gly Leu Leu Thr Leu Ala Lys Gly Lys Pro Ile Gly Lys Glu Gly
                435                 440                 445
Tyr Tyr Trp Leu Lys Ile His Gly Ala Asn Cys Ala Gly Val Asp Lys
                450                 455                 460
Val Pro Phe Pro Glu Arg Ile Lys Phe Ile Glu Glu Asn His Glu Asn
465                 470                 475                 480
Ile Met Ala Cys Ala Lys Ser Pro Leu Glu Asn Thr Trp Trp Ala Glu
                485                 490                 495
Gln Asp Ser Pro Phe Cys Phe Leu Ala Phe Cys Phe Glu Tyr Ala Gly
                500                 505                 510
Val Gln His His Gly Leu Ser Tyr Asn Cys Ser Leu Pro Leu Ala Phe
                515                 520                 525
Asp Gly Ser Cys Ser Gly Ile Gln His Phe Ser Ala Met Leu Arg Asp
                530                 535                 540
Glu Val Gly Gly Arg Ala Val Asn Leu Leu Pro Ser Glu Thr Val Gln
545                 550                 555                 560
Asp Ile Tyr Gly Ile Val Ala Lys Lys Val Asn Glu Ile Leu Gln Ala
                565                 570                 575
Asp Ala Ile Asn Gly Thr Asp Asn Glu Val Val Thr Val Thr Asp Glu
                580                 585                 590
Asn Thr Gly Glu Ile Ser Glu Lys Val Lys Leu Gly Thr Lys Ala Leu
                595                 600                 605
Ala Gly Gln Trp Leu Ala Tyr Gly Val Thr Arg Ser Val Thr Lys Arg
                610                 615                 620
Ser Val Met Thr Leu Ala Tyr Gly Ser Lys Glu Phe Gly Phe Arg Gln
625                 630                 635                 640
Gln Val Leu Glu Asp Thr Ile Gln Pro Ala Ile Asp Ser Gly Lys Gly
                645                 650                 655
Leu Met Phe Thr Gln Pro Asn Gln Ala Ala Gly Tyr Met Ala Lys Leu
                660                 665                 670
Ile Trp Glu Ser Val Ser Val Thr Val Val Ala Ala Val Glu Ala Met
                675                 680                 685
Asn Trp Leu Lys Ser Ala Ala Lys Leu Leu Ala Ala Glu Val Lys Asp
                690                 695                 700
Lys Lys Thr Gly Glu Ile Leu Arg Lys Arg Cys Ala Val His Trp Val
705                 710                 715                 720
Thr Pro Asp Gly Phe Pro Val Trp Gln Glu Tyr Lys Lys Pro Ile Gln
                725                 730                 735
```

```
Thr Arg Leu Asn Leu Met Phe Leu Gly Gln Phe Arg Leu Gln Pro Thr
                740                 745                 750

Ile Asn Thr Asn Lys Asp Ser Glu Ile Asp Ala His Lys Gln Glu Ser
            755                 760                 765

Gly Ile Ala Pro Asn Phe Val His Ser Gln Asp Gly Ser His Leu Arg
        770                 775                 780

Lys Thr Val Val Trp Ala His Glu Lys Tyr Gly Ile Glu Ser Phe Ala
785                 790                 795                 800

Leu Ile His Asp Ser Phe Gly Thr Ile Pro Ala Asp Ala Ala Asn Leu
                805                 810                 815

Phe Lys Ala Val Arg Glu Thr Met Val Asp Thr Tyr Glu Ser Cys Asp
            820                 825                 830

Val Leu Ala Asp Phe Tyr Asp Gln Phe Ala Asp Gln Leu His Glu Ser
        835                 840                 845

Gln Leu Asp Lys Met Pro Ala Leu Pro Ala Lys Gly Asn Leu Asn Leu
    850                 855                 860

Arg Asp Ile Leu Glu Ser Asp Phe Ala Phe Ala
865                 870                 875

<210> SEQ ID NO 3
<211> LENGTH: 884
<212> TYPE: PRT
<213> ORGANISM: Unknown
<220> FEATURE:
<223> OTHER INFORMATION: Description of Unknown: Enterobacteria
      phage T3

<400> SEQUENCE: 3

Met Asn Ile Ile Glu Asn Ile Glu Lys Asn Asp Phe Ser Glu Ile Glu
1               5                   10                  15

Leu Ala Ala Ile Pro Phe Asn Thr Leu Ala Asp His Tyr Gly Ser Ala
                20                  25                  30

Leu Ala Lys Glu Gln Leu Ala Leu Glu His Glu Ser Tyr Glu Leu Gly
            35                  40                  45

Glu Arg Arg Phe Leu Lys Met Leu Glu Arg Gln Ala Lys Ala Gly Glu
        50                  55                  60

Ile Ala Asp Asn Ala Ala Ala Lys Pro Leu Leu Ala Thr Leu Leu Pro
65                  70                  75                  80

Lys Leu Thr Thr Arg Ile Val Glu Trp Leu Glu Glu Tyr Ala Ser Lys
                85                  90                  95

Lys Gly Arg Lys Pro Ser Ala Tyr Ala Pro Leu Gln Leu Leu Lys Pro
            100                 105                 110

Glu Ala Ser Ala Phe Ile Thr Leu Lys Val Ile Leu Ala Ser Leu Thr
        115                 120                 125

Ser Thr Asn Met Thr Thr Ile Gln Ala Ala Ala Gly Met Leu Gly Lys
    130                 135                 140

Ala Ile Glu Asp Glu Ala Arg Phe Gly Arg Ile Arg Asp Leu Glu Ala
145                 150                 155                 160

Lys His Phe Lys Lys His Val Glu Glu Gln Leu Asn Lys Arg His Gly
                165                 170                 175

Gln Val Tyr Lys Lys Ala Phe Met Gln Val Val Glu Ala Asp Met Ile
            180                 185                 190

Gly Arg Gly Leu Leu Gly Gly Glu Ala Trp Ser Ser Trp Asp Lys Glu
        195                 200                 205

Thr Thr Met His Val Gly Ile Arg Leu Ile Glu Met Leu Ile Glu Ser
```

-continued

```
                210               215               220
Thr Gly Leu Val Glu Leu Gln Arg His Asn Ala Gly Asn Ala Gly Ser
225                 230                 235                 240

Asp His Glu Ala Leu Gln Leu Ala Gln Glu Tyr Val Asp Val Leu Ala
                245                 250                 255

Lys Arg Ala Gly Ala Leu Ala Gly Ile Ser Pro Met Phe Gln Pro Cys
            260                 265                 270

Val Val Pro Pro Lys Pro Trp Val Ala Ile Thr Gly Gly Tyr Trp
            275                 280                 285

Ala Asn Gly Arg Arg Pro Leu Ala Leu Val Arg Thr His Ser Lys Lys
    290                 295                 300

Gly Leu Met Arg Tyr Glu Asp Val Tyr Met Pro Glu Val Tyr Lys Ala
305                 310                 315                 320

Val Asn Leu Ala Gln Asn Thr Ala Trp Lys Ile Asn Lys Lys Val Leu
                325                 330                 335

Ala Val Val Asn Glu Ile Val Asn Trp Lys Asn Cys Pro Val Ala Asp
            340                 345                 350

Ile Pro Ser Leu Glu Arg Gln Glu Leu Pro Pro Lys Pro Asp Asp Ile
        355                 360                 365

Asp Thr Asn Glu Ala Ala Leu Lys Glu Trp Lys Lys Ala Ala Ala Gly
    370                 375                 380

Ile Tyr Arg Leu Asp Lys Ala Arg Val Ser Arg Ile Ser Leu Glu
385                 390                 395                 400

Phe Met Leu Glu Gln Ala Asn Lys Phe Ala Ser Lys Lys Ala Ile Trp
                405                 410                 415

Phe Pro Tyr Asn Met Asp Trp Arg Gly Arg Val Tyr Ala Val Pro Met
            420                 425                 430

Phe Asn Pro Gln Gly Asn Asp Met Thr Lys Gly Leu Leu Thr Leu Ala
        435                 440                 445

Lys Gly Lys Pro Ile Gly Glu Glu Gly Phe Tyr Trp Leu Lys Ile His
    450                 455                 460

Gly Ala Asn Cys Ala Gly Val Asp Lys Val Pro Phe Pro Glu Arg Ile
465                 470                 475                 480

Ala Phe Ile Glu Lys His Val Asp Asp Ile Leu Ala Cys Ala Lys Asp
                485                 490                 495

Pro Ile Asn Asn Thr Trp Trp Ala Glu Gln Asp Ser Pro Phe Cys Phe
            500                 505                 510

Leu Ala Phe Cys Phe Glu Tyr Ala Gly Val Thr His His Gly Leu Ser
        515                 520                 525

Tyr Asn Cys Ser Leu Pro Leu Ala Phe Asp Gly Ser Cys Ser Gly Ile
    530                 535                 540

Gln His Phe Ser Ala Met Leu Arg Asp Glu Val Gly Gly Arg Ala Val
545                 550                 555                 560

Asn Leu Leu Pro Ser Glu Thr Val Gln Asp Ile Tyr Gly Ile Val Ala
                565                 570                 575

Gln Lys Val Asn Glu Ile Leu Lys Gln Asp Ala Ile Asn Gly Thr Pro
            580                 585                 590

Asn Glu Met Ile Thr Val Thr Asp Lys Asp Thr Gly Glu Ile Ser Glu
        595                 600                 605

Lys Leu Lys Leu Gly Thr Ser Thr Leu Ala Gln Gln Trp Leu Ala Tyr
    610                 615                 620

Gly Val Thr Arg Ser Val Thr Lys Arg Ser Val Met Thr Leu Ala Tyr
625                 630                 635                 640
```

-continued

Gly Ser Lys Glu Phe Gly Phe Arg Gln Gln Val Leu Asp Asp Thr Ile
            645                 650                 655

Gln Pro Ala Ile Asp Ser Gly Lys Gly Leu Met Phe Thr Gln Pro Asn
        660                 665                 670

Gln Ala Ala Gly Tyr Met Ala Lys Leu Ile Trp Asp Ala Val Ser Val
    675                 680                 685

Thr Val Val Ala Ala Val Glu Ala Met Asn Trp Leu Lys Ser Ala Ala
690                 695                 700

Lys Leu Leu Ala Ala Glu Val Lys Asp Lys Lys Thr Lys Glu Ile Leu
705                 710                 715                 720

Arg His Arg Cys Ala Val His Trp Thr Thr Pro Asp Gly Phe Pro Val
                725                 730                 735

Trp Gln Glu Tyr Arg Lys Pro Leu Gln Lys Arg Leu Asp Met Ile Phe
            740                 745                 750

Leu Gly Gln Phe Arg Leu Gln Pro Thr Ile Asn Thr Leu Lys Asp Ser
        755                 760                 765

Gly Ile Asp Ala His Lys Gln Glu Ser Gly Ile Ala Pro Asn Phe Val
    770                 775                 780

His Ser Gln Asp Gly Ser His Leu Arg Met Thr Val Val Tyr Ala His
785                 790                 795                 800

Glu Lys Tyr Gly Ile Glu Ser Phe Ala Leu Ile His Asp Ser Phe Gly
                805                 810                 815

Thr Ile Pro Ala Asp Ala Gly Lys Leu Phe Lys Ala Val Arg Glu Thr
            820                 825                 830

Met Val Ile Thr Tyr Glu Asn Asn Asp Val Leu Ala Asp Phe Tyr Ser
        835                 840                 845

Gln Phe Ala Asp Gln Leu His Glu Thr Gln Leu Asp Lys Met Pro Pro
    850                 855                 860

Leu Pro Lys Lys Gly Asn Leu Asn Leu Gln Asp Ile Leu Lys Ser Asp
865                 870                 875                 880

Phe Ala Phe Ala

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtagggcacg tctacaagaa ag                                              22

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gttgagttgt tcctcaacgt ttttc                                           25

<210> SEQ ID NO 6
<211> LENGTH: 8
<212> TYPE: PRT
<213> ORGANISM: Unknown

```
<220> FEATURE:
<223> OTHER INFORMATION: Description of Unknown: Enterobacteria
      phage T7

<400> SEQUENCE: 6

Glu Glu Gln Leu Asn Lys Arg Val
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 7

His His His His His His
1               5
```